United States Patent [19]
Holcomb et al.

[11] Patent Number: 6,060,315
[45] Date of Patent: May 9, 2000

[54] METHOD FOR FACILITATING THE INTRODUCTION OF MATERIAL INTO CELLS

[75] Inventors: David E. Holcomb, Oak Ridge; Timothy E. McKnight, Greenback, both of Tenn.

[73] Assignee: Lockheed Martin Energy Research Corporation, Oak Ridge, Tenn.

[21] Appl. No.: 09/152,926

[22] Filed: Sep. 14, 1998

Related U.S. Application Data

[63] Continuation-in-part of application No. 08/982,195, Dec. 1, 1997.

[51] Int. Cl.$^7$ ............................ C12N 15/00; C12N 15/85; C12Q 1/68
[52] U.S. Cl. ........................... 435/446; 435/6; 435/173.5; 435/173.6; 435/173.7; 435/325; 435/358; 435/455; 435/461; 435/470; 435/471
[58] Field of Search ........................... 435/6, 173.1, 410, 435/173.4, 173.5, 325, 173.6, 463, 173.7, 243, 446, 455, 459, 461, 468, 470, 471, 354, 358

[56] References Cited

U.S. PATENT DOCUMENTS

| | | | |
|---|---|---|---|
| 4,822,470 | 4/1989 | Chang | 435/450 |
| 5,013,660 | 5/1991 | Kasuya et al. | 435/460 |
| 5,120,657 | 6/1992 | McCabe et al. | 435/285.3 |
| 5,149,655 | 9/1992 | McCabe et al. | 604/57 |
| 5,225,750 | 7/1993 | Higuchi et al. | 318/280 |
| 5,364,374 | 11/1994 | Morrison et al. | 604/272 |
| 5,371,003 | 12/1994 | Murry et al. | 800/292 |
| 5,466,587 | 11/1995 | Fitzpatrick-McElligott et al. | 435/459 |
| 5,538,877 | 7/1996 | Lundquist et al. | 800/265 |
| 5,538,880 | 7/1996 | Lundquist et al. | 800/265 |
| 5,550,318 | 8/1996 | Adams et al. | 800/300.1 |
| 5,554,798 | 9/1996 | Lundquist et al. | 800/300.1 |
| 5,610,042 | 3/1997 | Chang et al. | 800/288 |

OTHER PUBLICATIONS

Kraft, G. et al. Radiat Environ Biophys (1992).
The New Encyclopaedia Britannica, 15th Edition, vol. 25 (1994).

Theodore Friedmann, "Overcoming the Obstacles of Gene Therapy," *Scientific American*, Jun. 1997; pp. 96–101.

Hans Mohr and Peter Schopher, "Physiology of Crop Production," *Plant Physiology*, Springer–Verlag Berlin Heidelberg, 1995, p. 588.

Ileana Petcu, et al., "Kinetics of Electroinduced Pores as a Probe of Membrane Modification Produced by Ionizing Radiation," *Bioelectrochemistry and Bioenergetics*, 42 (1997), pp. 179–185.

Glenn F. Knoll, "Radiation Interactions," *Radiation Detection and Measurement*, Second Edition, John Wiley & Sons, Inc. (1989), pp. 30–51.

Eric J. Hall, *Radiobiology for the Radiologist*, J.B. Lippincott Co., Philadelphia ($4^{th}$ ed., 1994), pp. 3–13, 153–164.

Carl F. Perez et al, "DNA–Mediated Gene Transfer Efficiency is Enhanced by Ionizing and Ultraviolet Irradiation of Rodent Cells in Vitro," *Radiation Research*, 104 (1985), pp. 200–213.

*Primary Examiner*—George C. Elliott
*Assistant Examiner*—Mark L. Shibuya
*Attorney, Agent, or Firm*—Shelley L. Stafford

[57] ABSTRACT

The present invention is a method for creating a localized disruption within a boundary of a cell or structure by exposing a boundary of a cell or structure to a set of energetically charged particles while regulating the energy of the charged particles so that the charged particles have an amount of kinetic energy sufficient to create a localized disruption within an area of the boundary of the cell or structure, then upon creation of the localized disruption, the amount of kinetic energy decreases to an amount insufficient to create further damage within the cell or structure beyond the boundary. The present invention is also a method for facilitating the introduction of a material into a cell or structure using the same methodology then further exciting the area of the boundary of the cell or structure where the localized disruption was created so to create a localized temporary opening within the boundary then further introducing the material through the temporary opening into the cell or structure.

40 Claims, 7 Drawing Sheets

METHOD FOR FACILITATING THE INTRODUCTION OF MATERIAL INTO CELLS

CROSS-REFERENCED APPLICATIONS AND PATENT'S

The present application is a Continuation-In-Part Application of co-pending U.S. patent application Ser. No. 08/982,195, filed Dec. 1, 1997, incorporated herein by reference.

This invention was made with Government support under contract DE-AC05-96OR22464 awarded by the U.S. Department of Energy to Lockheed Martin Energy Research Corporation, the Government has certain rights in this invention.

FIELD OF THE INVENTION

The present invention relates to a method for creating a highly localized disruption within a boundary of a cell or structure by exposing the cell or structure to energy-regulated ionizing particle radiation, particularly a method for facilitating the introduction of material into cells or structures by exposing the cell or structure to energy-regulated ionizing particle radiation to create a highly localized disruption within the cell or structure boundary and further exciting the cell where the localized disruption was created so to create a localized temporary opening within the cell for the introduction of material.

BACKGROUND OF THE INVENTION

The inability to effectively transform organisms through integration of desirable genetic information into the genome of cells is a significant limitation to genetic research, acting as a bottleneck to the otherwise rapidly developing field of biotechnology. A June 1997, *Scientific American* article "Overcoming the Obstacles of Gene Therapy" by Theodore Friedmann, focuses on the current limitations of cellular genetic transformation which predominantly arise from the inability to effectively administer genetic transformation vectors into cells. The article addresses the limitations of cellular genetic transformation as applied to medicine, indicating that, by overcoming these obstacles, gene therapy, or the admission of specific genes to cells for the purpose of treating disfunction, has the potential to revolutionize medical science. The National Institutes of Health (NIH) have recognized the potential of gene therapy and have given it priority among their areas of scientific interest.

The genetic transformation of economically significant crops is also a major biotechnology research thrust area. The ability to transform crops for improved productivity, enhanced quality, resistance to climate, pests, and herbicides, and extended climatic range is an important pursuit in providing for an expanding world population.

Cellular transformation is important to many other industrial sectors. Production of pharmaceuticals through transformation biotechnology is an emerging focus area. Plant, mammalian, and bacterial colonies are genetically transformed to produce desired pharmaceuticals and pharmaceutical precursors. Chemical producing bioreactors using transformed organisms as production units are also emerging as a significant component of this industrial sector.

Current methods for cellular transformation focus on the delivery and genomic incorporation of transformation vectors to target cells. These genetic vectors may take a variety of forms, but are typically double stranded or single stranded "naked" DNA sequences or bacterially derived, plasmid vectors. The latter are short (typically 2—10 kbase) circular DNA sequences which contain complete gene sequences, promoters, enhancers, restriction sites to enable further genetic manipulation of the plasmid, and other advantageous segments such as reporter genes for indication of when a transformation event has occurred. Introduction of these vectors into a cell, through the cell boundary, may result in transient expression of the inserted genes, and may ultimately stably transform the target cell by insertion of the delivered gene sequences into the host genome.

Delivery of transformation vectors to cells is accomplished in a variety of ways. The effectiveness of each method varies widely with cell type. For dicotyledonous plant cells, effective vector delivery may be performed using an agrobacterium vector, which infects the cells of the host plant, and subsequently delivers plasmid DNA to the infected cells. This method has limited application to various stages of growth of dicotyledonous cells, and is significantly limited in application to monocotyledonous plants, including the agronomically significant cereals. This latter limitation arises because few monocotyledonous plants are natural hosts for agrobacteria. Therefore, recent research activity has focused upon alternative methods for transforming this sector of the plant kingdom.

Similar viral transformation techniques exist for mammalian cells, with an underlying limitation that most of these infectious techniques are specific to certain cell types, and fundamentally lack applicability to a wider group of cell types.

A variety of mechanical methods have been developed to overcome the specificity of infectious transformation techniques. These methods, not being limited to infectious pathways, are designed to provide transformation techniques to a wide array of cell types. Methods include electroporation, microinjection, DNA application into the budding stage of flowering plants, laser- or opto-poration, microprojectile bombardment and whisker-mediated transformation. Essentially, each of these methods employs a mechanical means to damage the cell and its cellular boundary to facilitate the introduction of foreign DNA into the cell. In each of these methods, efficiency is often very low, and often the gene expression is only transiently manifested. Further, these methods are not ideally suitable for continuous-processing systems. Electroporation, employs a, or a series of, electrical pulses to (typically) a cellular suspension, which creates transient, electrically-induced pores in the cell membrane through which vectors may be introduced. Microinjection employs a precisely controlled microscale needle to puncture the cellular membrane and deliver vectors into the cell. Laser-or opto-poration creates chemical, electrical and thermal gradients around a target cell, opening the cell and facilitating the transport of genetic material into the cell. Microprojectile bombardment utilizes a variety of methods to ballistically fire vector-coated particles through cellular boundaries, to facilitate either directly or indirectly, the introduction of vectors into the cell. For example, Chang et al have developed a technique for delivering plant transformation vectors using microprojectile bombardment. In their technique, small metal particles on the order of 0.5–5 $\mu$m are coated with plasmid vectors and accelerated via various methods through the cellular boundary. Those that remain within the host cell shed their DNA coating, that in turn may be transcribed for expression of delivered genes. This delivery mechanism, although well suited to laboratory studies, is recognized as being highly inefficient, and is currently unsuitable for continuous-feed bioreactor implementation. One of the problems with this method is that although in some instances, the coated vectors are delivered to a cell and may promote transformation of that cell, often, the microprojectile travels through the cell without effective plasmid delivery. Further, the assault of the projectile is often too damaging for the cell to recover, resulting in cell death.

A fundamental limitation of existing transformation methodologies is the inability to precisely control genetic vector delivery, and the associated damage created by the method. For instance, optimal electroporation protocols are a fine balance between effective plasmid delivery, and the destruction or loss of viability of cells due to excessive damage during the electroporation procedure. The pores created are often too large and cannot be resealed; or fail to close quickly enough to prevent excessive influx of surrounding media into the cells, resulting in cell swelling and death. Similarly, laser- or opto-poration is highly damaging, with the fundamental focal limitation of light being too large to produce acceptably small pores. Further, laser excitation produces a columnar destruction path which is not limited to the boundary of the target cell. Along this destruction path, heat and the production of free radicals may destroy the cell nucleus, surrounding plasmid vectors, and ultimately the cell itself. The damage of microprojectile bombardment is also fundamentally uncontrolled. Ballistic particles may excessively disrupt both cell internal structures as well as cellular boundaries, destroying viability of cells along their destructive path.

Slow processing rate, low transformation efficiency, lack of general applicability, and excessive damage limit the effectiveness of all present cellular transformation mechanisms. Current methodologies rely upon either natural biological mechanisms or coarse, mechanically-based means of administering genetic material into target cells. Mechanically based methods are extremely damaging and result in very low transformation rates, and are quite costly. The biological methodologies, employing bacterial or viral infection as the transformation mechanism (i.e. transfection), are only narrowly applicable, working selectively on organisms that act as hosts to the infective vector.

In 1985, Perez et al indicated in *Radiation Research* that ionizing and ultraviolet irradiation of rodent cells increases the efficiency of stable transformation of these cells. The mechanism of this increase in efficiency is the creation of radiation-induced lesions within the genomic DNA of these cells to provide sites for incorporation of transformation vectors thereby increasing the probability of stable transfection. Perez et al's methodology uses unregulated radiation to create lesions in the genomic DNA to facilitate incorporation at these lesion sites of previously delivered genetic material. Perez et al do not address delivery of material into cells at all. Particularly, Perez et al do not employ energy-regulated radiation to create localized stress sites within the cellular boundary to facilitate genetic material into the cell. Moreover, Perez et al's methodology intentionally damages the cell, including the contained genomic DNA, to facilitate genomic incorporation of previously delivered genetic material.

Traditional discussions of linear energy transfer (LET) and relative biological effects (RBE) of alpha-particles and other ionizing radiations focus on the potential for ionizing radiation to damage the functionality of a cell through directly ionizing effects and the generation of free-radicals which in turn damage the internals of a cell. Hall, incorporated herein by reference, indicates in *Radiobiology for the Radiologist* (4$^{th}$ ed., J. B. Lippincott Company 1994) that a LET of 100 keV/$\mu$m is optimal in terms of producing a biological effect on a cell. Due to natural DNA repair mechanisms and the redundancy of the double helix, manipulation of or damage to chromosomal DNA is maximized when both strands of the DNA helix are damaged directly across from each other. 100 keV/$\mu$m is maximally efficient for damaging both strands of the double helix, as this LET corresponds to ionizing events at roughly 2 nm intervals, the width of the double helix. Hall further indicates that " . . . much more densely ionizing radiation . . . will readily produce double strand breaks, but energy will be wasted because the ionizing events are too close together. 'RBE is the ratio of doses to produce equal biological effect'" Thus, the most efficient LET to affect the entire cell (i.e. through chromosomal damage) is that which corresponds to 2 bond breakages in a 2 nm pathlength, or 100 keV/$\mu$m.

OBJECTS OF THE INVENTION

Accordingly, it is an object of the present invention to provide an effective method for creating a localized disruption within a boundary of a cell or structure.

It is also an object of the present invention to provide an effective method for facilitating the introduction of material into cells and structures.

It is another object of the present invention to provide an effective method for facilitating the introduction of pharmaceuticals into viable cells.

It is yet another object of the present invention to provide an effective method for facilitating the introduction of genetic material into viable cells for the purposes of cellular transformation.

It is still yet another object of the present invention to provide a means to increase the efficiency of existing transformation methodologies by providing a mechanism to reduce the damage created by said existing transformation methodologies.

It is another object of the present invention to provide an effective, controlled method for facilitating the introduction of material into cells or structures by creating a highly localized stress site within the cell or structure boundary, with the aim of focusing concurrent or subsequent manipulation of the boundary of the cell or structure to the stress site.

It is a further object of the present invention to provide an effective, controlled method for facilitating the introduction of material into cells or structures that is highly localized by exposing the cell or structure to energy regulated ionizing particle radiation, thereby rearranging the atomic bonds in a localized region of the cell or structure boundary, thereby inducing stress at the localized region, thereby increasing the chemical, mechanical, electrical reactivity of the region, thereby reducing the energy requirements of concurrent or subsequent manipulation of the region, wherein the manipulation is used to increase fluidity of the region by providing a pathway for the influx of the material into the cell or structure through the region, whereby the reduction in energy requirement increases the efficiency of the material introduction.

It is yet a further object of the present invention to provide an effective, controlled method for facilitating genetic material introduction into viable cells that is highly localized by exposing the cell to energy regulated ionizing particle radiation, thereby rearranging the atomic bonds in a localized region of the cell boundary, thereby inducing stress at the localized region, thereby increasing the chemical, mechanical, electrical reactivity of the region, thereby reducing the energy requirements of concurrent or subsequent manipulation of the region, wherein the manipulation is used to increase fluidity of the region by providing a pathway for the influx of the genetic material into the cell through the region, whereby the reduction in energy requirement increases the efficiency of the genetic material transport, and the reduction in energy requirement decreases trauma to the viable cell and increases viability of cells subjected to the manipulation.

Further and other objects of the present invention will become apparent from the description contained herein.

SUMMARY

In accordance with one aspect of the present invention, the foregoing and other objects are achieved by a method for creating a localized disruption within a boundary of a cell or structure comprising the steps of first, generating a set of energetic charged particles; then, exposing a boundary of a cell or structure to the set of energetic charged particles, while regulating the energy of the charged particles so that the charged particles have an amount of kinetic energy sufficient to create a localized disruption within an area of the boundary of the cell or structure, then upon creation of the localized disruption, the amount of kinetic energy decreases to an amount insufficient to create further damage within the cell or structure beyond the boundary.

In accordance with another aspect of the present invention, other objects of the invention are achieved by a method for introducing a material into a cell or structure comprising the steps of first, generating a set of energetic charged particles; secondly, exposing a boundary of a cell or structure to the set of energetic charged particles, while regulating the energy of the charged particles so that the charged particles have an amount of kinetic energy sufficient to create a localized disruption within an area of the boundary of the cell or structure, then upon creation of the localized disruption, the amount of kinetic energy decreases to an amount insufficient to create further damage within the cell or structure beyond the boundary; thirdly, disposing the material proximal to the cell or structure in a form suitable for penetrating the area of the boundary where the localized disruption occurred; fourthly, exciting the area of the boundary of the cell or structure where the localized disruption was created so to create a localized temporary opening within the boundary; and then, introducing the disposed material through the opening into the cell or structure.

In accordance with yet another aspect of the present invention, other objects of the present invention are achieved by a method for stably, genetically transforming a cell comprising the steps of first, generating a set of energetic charged particles; secondly, exposing a boundary of a cell to the set of energetic charged particle, while regulating the energy of the charged particles so that the charged particles have an amount of kinetic energy sufficient to create a localized disruption within an area of the boundary of the cell, then upon creation of the localized disruption, the amount of kinetic energy decreases to an amount insufficient to create further damage within the cell beyond the boundary; thirdly, disposing gentic material proximal to the cell in a form suitable for penetrating the area of the boundary where the localized disruption occurred; fourthly, exciting the area of the boundary of the cell where the localized disruption was created so to create a localized temporary opening within the boundary; and finally, introducing the genetic material through the opening into the cell.

BRIEF DESCRIPTION OF THE DRAWINGS

For a better understanding of the present invention, together with other and further objects, advantages and capabilities thereof, reference is made to the following disclosure and appended claims when read in connection with the appended drawings, wherein:

DETAILED DESCRIPTION OF THE INVENTION

Figure 1:
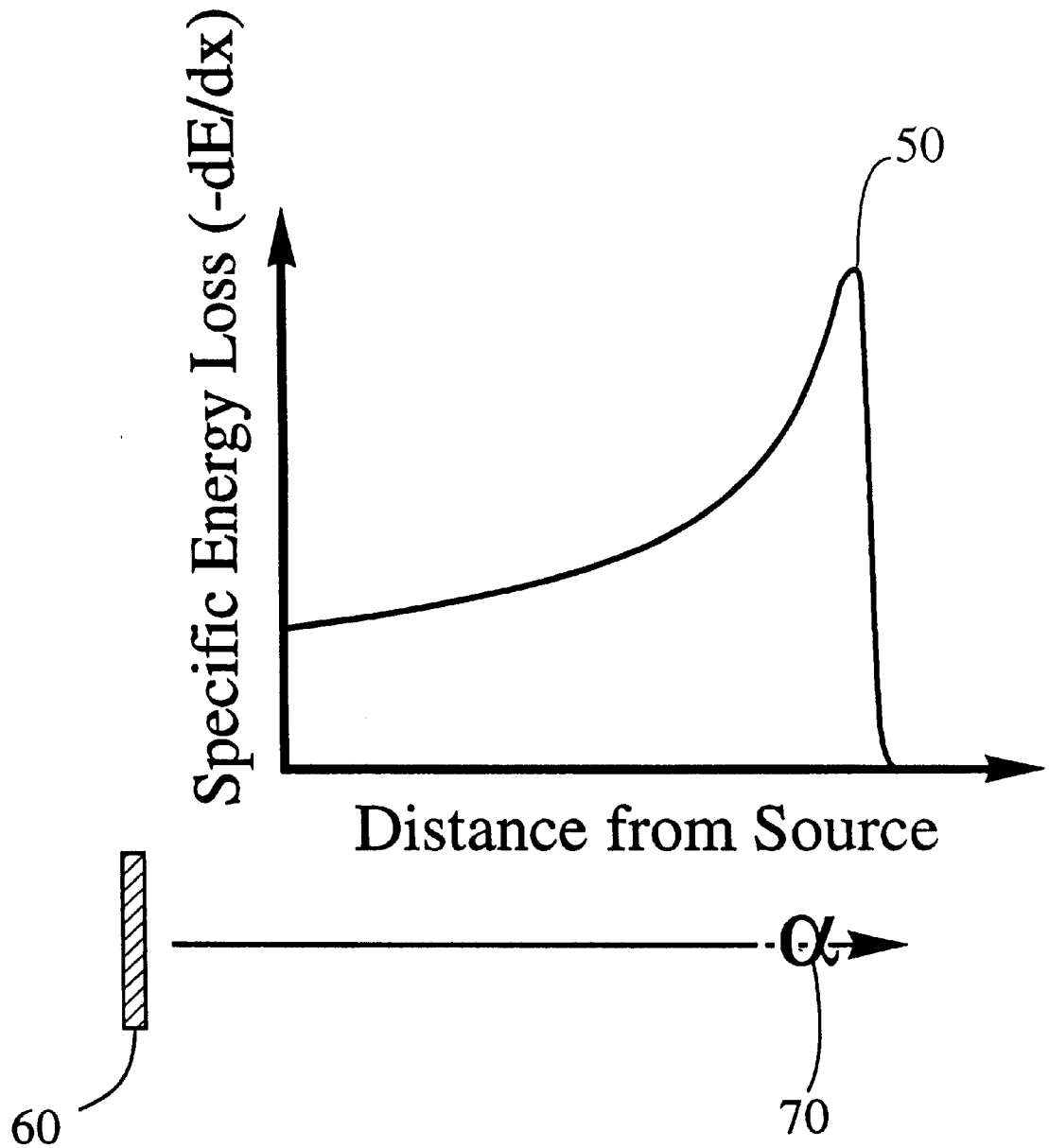
FIG. 1 illustrates a Bragg Curve showing the specific energy loss along the track of the alpha particle, indicating a position of maximum disruption at the tail end of the total alpha particle range.

Applicant's invention overcomes these problems of damaging the cell as well as the cell's contained genomic DNA by employing energy-regulated radiation to create localized disruptions or stress sites within the cellular or structural boundary to facilitate material delivery into the cell or structure.

The subject invention is a new method for facilitating the introduction of foreign material into cells or structures that uses an energy-regulated ionizing particle radiation to cause highly localized atomic bond rearrangement within the boundary of the cells and structures, without imparting significant additional damage to the region beyond the boundary. The rearrangement of bonds induces mechanical stress at the localized region of the boundary due to reformation of bonds in a randomized manner which destroys the pre-irradiated, stable energy configuration of the boundary layer bonds. This stress increases the chemical, mechanical, electrical reactivity of the disrupted region, thereby focusing and therefore reducing the energy requirements of concurrent or subsequent manipulations to the disrupted region. The manipulations may be used to increase fluidity of the disrupted region by creating transient openings at this region (also known as the stress site). These openings provide a pathway for the influx of foreign material into the cell or structure through the disrupted region. This creation of a stress site within the cell or structure boundary enables or facilitates the use of current conventional electrical, chemical, mechanical or biological material delivery means such as electroporation, ultrasonic excitation, mechanical agitation, chemical etching, bacterial transfection, viral transfection, etc. to be used with higher efficiency because it lowers the energy requirement of these methods. For example, electroporation creates membrane pores by the application of an electric potential across the cellular boundary. Normally, this potential opens pores to allow material fluidic transport across the cell membrane, but it often rips open cells, causing extensive damage. The method of the present invention provides radiation which imparts a local sensitivity which focuses concurrent and subsequent damage. For concurrent electroporation, this focusing means less electroporation voltage is necessary enabling the damage site to be transiently opened in a much more controlled manner, i.e. membrane pores are enlarged as opposed to membrane itself being ripped open. Due to the decreasing of overall cell damage, the site has a higher probability of resealing following material delivery, which allows the cell to continue to develop. The detail of this aspect of the present invention is validated in *Bioelectrochemistry and Bioenergetics*, "Kinetics of Electroinduced Pores as a Probe of Membrane Modification Produced by Ionizing Radiation" by Ileana Petcu et al, incorporated herein by reference.

In applicant's invention, "structure" refers to any region surrounded by a boundary layer with mechanical functionality (i.e. resistance to deformation, tensile strength, mechanical stability, chemical resistance) determined by the ordered arrangement of the atomic bonding within the boundary layer. In addition to the cellular boundaries of membranes and cell walls, the use of the term "structure" provides the application of the methodology to other bounded regions including liposomes, cell nuclei, cell organelles, pollen, bacterial cell walls, living and dead cellular husks, viruses and viral particles, protein coated particles (capsids), sperm and egg cells. All of the boundary structures of these entities are subject to atomic bonding rearrangement via irradiation with ionizing radiation particles, and therefore are subject to the formation of mechanically, chemically, and electrically sensitized regions which may he exploited to increase the fluidity of the boundary at a very localized region. An example of a non-subject entity is a water droplet, which does not feature a boundary comprised of a matrix of organized atomic bonds. Therefore, ionization of the water droplet boundary does not produce a randomized, localized rearrangement of bonds.

In the present invention, a cellular or structural boundary is defined as the cell membrane/cell wall for plants, the cell membrane for animal cells and any other boundary in which a cell or structure is contained.

In applicant's invention, "energy-regulated" refers to the purposeful control of the amount of energy of an ionizing radiation particle. Energy regulation may be realized by either reducing or increasing the energy of an ionizing radiation particle to a desired level. In applicant's invention, energy is removed by directing the particle through an energy absorbing media. The energy-regulating layer decreases the kinetic energy of the particle. For example, the preferred energy regulation for alpha sources is when the alpha particle travels through an energy-regulating layer or coating being of a thickness such that the end of the particle range occurs within or just beyond the boundary of the cell or structure. For accelerated ions, the preferred method of energy regulation is controlling the amount of acceleration of the particle such that the particle end of range occurs within, or just beyond, the boundary of the cell or structure. An energy-regulating layer could be any media between the cell or structure and the radiation source being of a sufficient thickness as to attenuate the energy of the radiated particle so that its range extends only through the cellular or structural boundary. For ionizing particle radiation, the reduction of energy is determined by the speed of the ionizing particle, its charge, and the electron density of the absorbing media through which the particle travels. For a given charged particle of known energy, such as an alpha ($\alpha$)-particle, the desired reduction in energy is practically performed by setting the thickness of the absorbing media. Energy regulation may also be accomplished by increasing the energy of the ionizing particle, i.e. accelerating a charged particle. There are other forms of charged particle radiation other that alpha particles that may be implemented in the present invention. These other forms of charged particle radiation include beta particles, heavy and light ions, and positrons. Those skilled in the art should also realize that these particle radiations may be generated in a variety of ways including ion acceleration, spontaneous decay of isotopes, use of indirectly ionizing radiation to create directly ionizing particle radiation, fission products, and electron guns.

The methodology of applicant's invention has been demonstrated to increase the efficiency of introduction of plasmid genetic vectors (green fluorescent protein pGreen Lantern-1,5031 bp) into cells using subsequent electroporation of irradiated cells. Those skilled in the art will recognize through the following discussion that this methodology is also suited to cellular introduction of other similarly sized and smaller materials, including other plasmid vectors, nucleic acids, and other macromolecules, including pharmacologically active compounds, labeling dyes, proteins and enzymes, carbohydrates and lipids.

It is imperative with Applicant's invention that it be realized the potential for cellular damage using the radiation mechanisms as described above. Therefore, it is the express intent of Applicant's invention to minimize the biological effect to cells with regard to that caused by radiation damage. This is why radiation damage is intentionally controlled to only occur to the cellular boundary, such that internal ionization events, and the production of free-radicals internally in the cell is minimized. By minimizing internal cellular damage, Applicant's method maintains the highest cellular viability, allowing normal cellular physiology.

Figure 2:
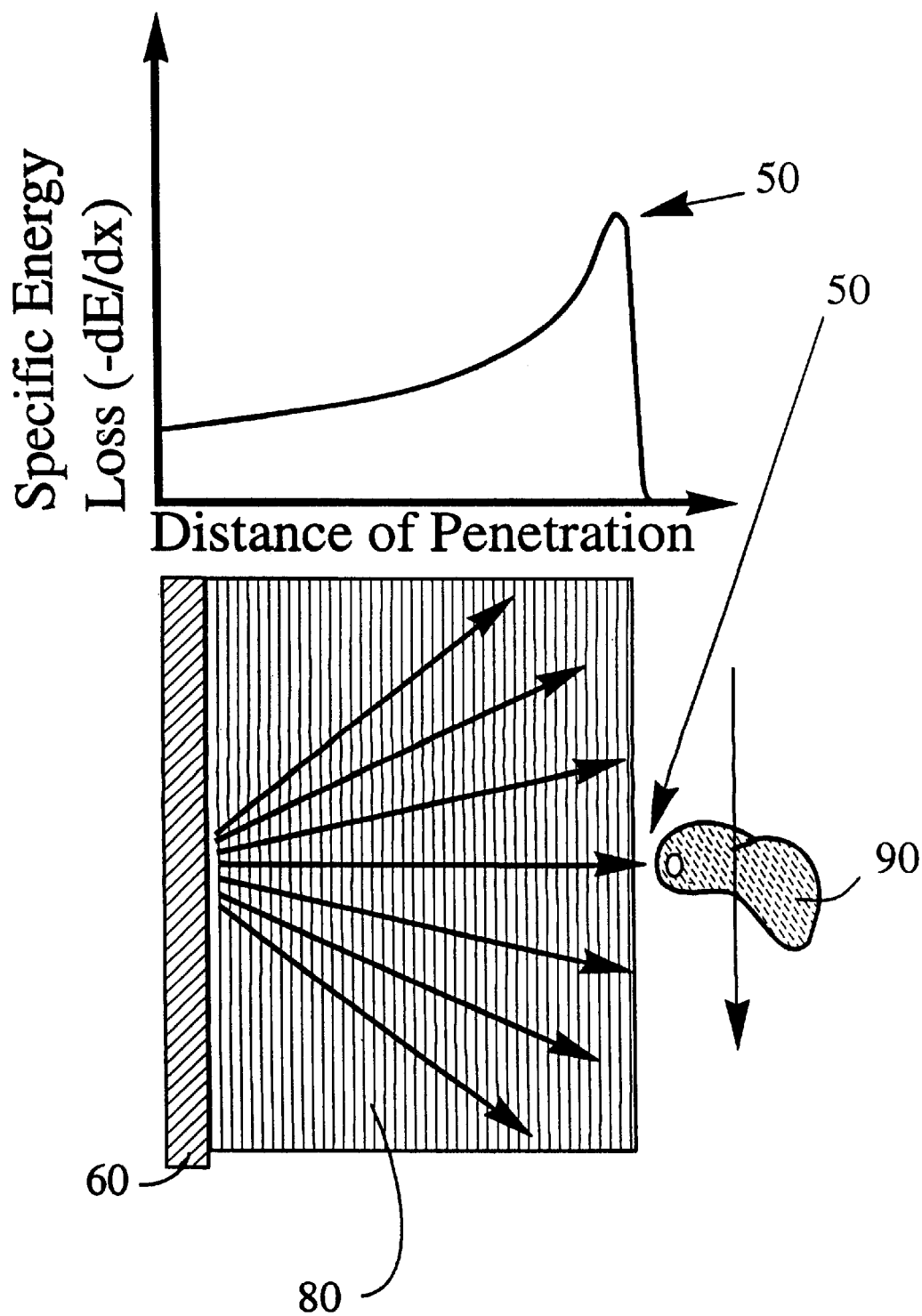
FIG. 2 illustrates that internal damage to the cells or structures can be avoided by coating the alpha emitter with a thin energy-regulating layer, tailored such that the maximum energy transfer portion and end of the alpha particle range occurs just beyond the layer boundary.

Energy dissipation theory for alpha particle interactions with biological systems is well understood, and the location of disruption activity may be precisely controlled. Within aqueous media and biological tissue, the range of isotopically derived alpha particles, (such as Am-241) with energies of several MeV is approximately 10–50 $\mu$m, with a large fraction of energy deposited towards the end of this range, designated as reference numeral 50 in FIG. 1. Shortly beyond this distance, alpha particle energy dissipation and associated damage drops effectively to zero, as illustrated in FIG. 1. FIG. 1 illustrates the pathway or particle range of alpha particles 70 once they are emitted from the alpha emitter source 60, the alpha particles loose energy over distance from the source until they reach their limited distance at the position of maximum energy transfer 50, then the alpha particle energy dissipation and associated damage drops effectively to zero. Alpha particles interact with matter primarily through the Coulomb interactions between their positive charge and the negative charge of the orbital electrons in the absorbing matter. Alpha particles simultaneously interact with many electrons. In any one such encounter, the alpha particle may transfer enough energy to raise the electron to a higher orbit (excitation) or completely remove the electron (ionization). Collision kinetics limit the maximum amount of energy which can be transferred in any one collision. Since alpha particles interact simultaneously with many electrons, the net effect is to continuously slow the alpha particle. Another consequence of this is that alpha particles have sharply defined travel distances referred to as the particle range. The linear rate of energy loss for charged particles, including alpha particles, in an absorber is given in the Bethe formula as:

$$-\frac{dE}{dx} = \frac{4\pi\sigma^4 z^2}{m_0 v^2} N \left( Z \left[ \ln \frac{2m_0 v^2}{I} - \ln\left(1 - \frac{v^2}{c^2}\right) - \frac{v^2}{c^2} \right] \right)$$

where v and z are the velocity and charge of the primary particle, N and Z are the number density and atomic number of the absorber atoms, $m_0$ is the electron rest mass, and e is the electronic charge. The parameter I represents the average excitation and ionization potential of the absorber. This is described by Glenn F. Knoll, 1989, *Radiation Detection and Measurement* (Chapter 2), incorporated herein by reference. As the particle slows down, it spends more time in the vicinity of absorber atoms and hence interacts more strongly with them. The net result of this is that alpha particles deposit a large fraction of their energy at the end of their range. A plot of the specific energy loss along the track of the alpha particle 70, the Bragg curve shown in FIG. 1, is provided indicating a position of maximum disruption 50 at the tail end of the total alpha particle range. At the tail end of the range, the alpha particle acquires electrons from the absorber, becoming a helium atom within the absorber. At this point, the helium atom generates no further damage. Thus, the damage pathlength of an ionizing radiation particle is limited in range. Internal damage to the cells or structures can be avoided by coating the alpha emitter source 60 with a thin energy-regulating layer 80, as seen in FIG. 2, tailored such that the maximum energy transfer 50 portion of the alpha particle range occurs just beyond the layer boundary. In FIG. 2 the tracks of the alpha particles emerging from the alpha source are shown as arrows. Only those alpha particles emerging from one location of the alpha source are displayed in the figure for clarity. By appropriate positioning of cells 90, structures 90 and genetic transformation vectors 90, for example, suspended within an aqueous medium to create a cell or structure flow 90, geometries may be established such that the highest disruption activity occurs within the boundary of the cell or structure. The localized disruption to the cell or structure boundary provides a localized stress concentration site which is used as a controlled "gate" allowing easier opening of the cell or structure to permit transient influx of neighboring plasmid vectors. Since the alpha induced disruptions are extremely small, the cell may subsequently heal following vector delivery. The cell or structure then continues to develop, including possible genomic insertion of delivered plasmid gene sequences and reproduction of transgenic cells.

In addition to ionizing particle radiations being limited in range, their damage path is also limited in diameter. Alpha particles interact with a narrow column of material (delta ray pathlength ~5 nm) until near the end of their range where they slow down sufficiently to interact more strongly with target material electrons due to longer interaction times. At this point, they begin to interact directly with the target material lattice atoms through elastic collisions (alpha energy becomes less than necessary to excite outer electrons, ~4 keV). At this point, disruptive activity of the particle is enhanced, causing a localized region of much higher damage. In alpha-track detecting materials, used to visualize radiation damage, typical teardrop shaped damage paths illustrate this end-of-track disruptive behavior.

Along the destructive path of the ionizing radiation particle, atomic bonds are disrupted and reform in a randomized manner. This randomization creates stresses throughout the damage path. These stresses increase the chemical, electrical, and mechanical reactivity of the damaged region. In alpha track detecting materials, following irradiation, the detecting material is etched in a strong base in order to reveal the alpha track damage paths. Preferential chemical etching occurs along the damage paths due to the increase in chemical reactivity of these regions induced by bond randomizations. Damage tracks become so enlarged through this etching process, that they may be visualized using optical microscopy. Similarly, the damaged region becomes more reactive to electromechanical manipulations. Petcu et al, previously incorporated by reference, have demonstrated that creation of damage sites with beta-particles makes these localized damaged regions have higher fluidity during electroporation. The induction of stress along the beta-particle damage site provides for larger pores during the electroporation process, and increases the resealing rate of these pores following electroporation pulses. Larger sized pores provides for the introduction of larger molecules into the cell. This increased resealing rate provides for less trauma to the cell and thus higher cell viability after the electroporation process. Therefore, by limiting damage to the boundary of target cells and structures, the internals of the cell or structure may be protected while boundary damage regions are created which become more reactive to concurrent and subsequent electrical, chemical, and mechanical manipulation. This increase in reactivity reduces the energy requirements of the chemical, electrical and mechanical manipulations and serves to increase the efficiency of material delivery using these methods. Further, by reducing the energy requirements, and thus trauma, to cells experiencing these material delivery methods, cell boundary damage is reduced and cell viability is increased during the concurrent or subsequent material delivery.

As mentioned above, in some instances, end-track damage will not be of sufficient magnitude to enable unassisted vector transport through the disrupted path. Some chemical, mechanical, electrical or biological assistance may be required to enlarge the smaller, alpha-induced disruptions to adequate size for plasmid transport, on the order of or about 0.1–1.0 $\mu$m. Several mechanisms are possible, including concurrent use of surface acoustic waves, or chemical disassociation techniques. The key, however, is to induce small disruptions in the membrane with an energy-regulated ionizing particle radiation such as alpha particles, sensitizing the cellular or structural boundary to concurrent or subsequent chemical/electrical/mechanical techniques. The advantage to the present invention is that the alpha-induced disruption, and subsequent rearrangement of bonds, causes highly localized stress sites within the boundary of the cell or structure, greatly reducing the energy required to further disrupt (i.e. open) the cell or structure boundary for subsequent material delivery. Good analogies for this sensitization are cellulose (of which cell and structure boundaries as cell walls are predominantly comprised) and polycarbonate-based radiation track detectors, that typically show large (with respect to cellular dimensions) diameter etch tracks on the level appropriate for plasmid transport. Preferential etching along the alpha-damage path is promoted due to the localized bonding disruption caused along the alpha-damage path. Alpha particle induced disruption prepares the cell for well-controlled, concurrent use or subsequent use of other disruptive techniques, enabling highly controlled delivery of genetic transformation vectors.

Concurrent or subsequent material delivery techniques are then used to transport or deliver material into the cells and structures. Once damage sites are created in cells or structures, the material to be delivered must be forced into that cell or structure using the damage site at a region of vulnerability (stress site). For some materials, natural mobility due to concentration gradients may be sufficient to open the damage site and admit material. For large particles, however such as plasmids, the plasmids may need to be actively forced into the cell or structure using such electrical, chemical, mechanical or biological means such as electroporation, ultrasonic excitation, mechanical agitation, chemical etching, bacterial transfection, viral transfection, etc.

For small molecules, the disruption in a structure boundary caused by radiation damage and subsequent natural conditions about the damage site may be sufficient to promote small molecule material delivery into the cell. For larger molecules, such as plasmids that are roughly 1 $\mu$m in diameter, additional manipulation of the damage site may be required in order to provide a larger opening in the cell for material transport. Concurrent and subsequent boundary manipulations to deliver material through the disrupted region may include a variety of chemical, electrical and mechanical techniques. Traditional transformation methods most suited to exploiting the sensitized properties of the disrupted region include electroporation. For plant and bacterial cells, that feature a rugged cell wall, the irradiation may be used to produce regions of high chemical reactivity within the cell wall. Enzymes and other chemicals may then be used to preferentially etch the damage tracks through the cell wall. Subsequent electroporation may then be used to deliver genetic material to the cell through tunnels created in the partially digested cell wall. Those skilled in the art will recognized that plant cell walls, comprised predominantly of cellulose, will behave similar to cellulose-based track recorders, and may be preferentially etched along the damage paths of irradiated regions. Those skilled in the art of plant physiology will recognize that protoplasting techniques are used to digest the cell wall from plants to facilitate the use of electroporation to the resultant protoplast plant cell. Full protoplasting of plant cells often reduces their viability, and therefore the ability to only partially protoplast a cell wall by preferentially etching along a radiation damage path to create tunnels for electroporation provides for reduction of cell mortality.

In addition to increased mechanical, electrical, and chemical reactivity of the damage site, surface modifications at the damage site and wound responses of the cell may also promote infectious pathways for bacterial and viral attack. Thus, this method may also facilitate material delivery through these mechanisms by providing increased levels of infectious attack.

As the local atomic bonding disruption ability of alpha particles within biological systems is extremely high, and as their damage can be limited to a highly localized region, alpha particles are ideal candidates for local disruption of structure boundaries with the purposeful avoidance of related internal structural damage. Boundary disruption of target structures may be achieved while avoiding internal damage to the structures by positioning the structure boundaries within close proximity to the end-track of an alpha particle's travel. Such positioning provides for the highest amount of energy deposition per unit distance into the boundary by the alpha particle, while minimizing the potential for further internal structural damage by the alpha particle. For the application of genetic transformation of cells, wherein genetic material is delivered through the cellular boundary and into a cell, this limitation of internal damage is vital. In generating a localized boundary disruption through which genetic material is or will be introduced, it is crucial that subsequent internal damage to a viable cell does not occur in order that the cell remains viable such that it may become genetically transformed.

Appropriate placement of target cells at the end-track of alpha particle travel may be accomplished in a variety of ways. A practical method, and the preferred embodiment of applicant's invention, employs an isotopic source of alpha particles which has been coated with an energy absorbing material in order to regulate the energy of alpha particles such that the end-track of alpha particle travel occurs just slightly beyond the coating surface, and ideally at the interior side of the cellular or structural boundary that is adjacent to the alpha source. Cells may be positioned against this surface in a variety of ways, and held in position for a given amount of time in order to allow alpha particle impingements at the cellular boundary which is held against the absorbing material surface. Each alpha impingement on the cellular boundary creates one localized region of disrupted bonds, sensitizing this region to concurrent or subsequent manipulations for the purpose of material delivery through that region. The longer the cell is held in place, the more alpha particle impingements occur on the cellular boundary and the more localized damage sites are created. Each damage site that is created lowers the energy requirement of concurrent or subsequent manipulations to that cell for purposes of material delivery.

The following EXAMPLE 1 is a specific methodology and the preferred embodiment for inducing localized disruption in Chinese Hamster Ovary (CHO) cells which in turn are used to increase the efficiency of introduction of plasmid vectors into the cells using electroporation. This methodology has been shown to increase delivery of the Green Fluorescent Protein (GFP) plasmid vector (Gibco BRL, pGreen Lantern-1,5031 base pairs) to CHO cells by a factor of approximately 2x.

EXAMPLE 1

For this methodology, CHO cells (CHO-$K_1$, ATCC CCL61, available from the American Type Culture Collection at 12301 Parklawn Dr., Rockville, Md. 20852) were cultured and placed in suspension, in growth media, in dishes constructed with a bottom surface of 12.7 $\mu$m polyester film (DuPont, Mylar™ film). A Curium-244 (Cm-244) source from Isotope Products produced alpha emissions at 5.81 MeV (77%) and 5.77 MeV (23%). The Curium-244 source was made with a thin titanium coating to fix the curium. The polyester film of 12.7 $\mu$m thickness, acting as the dish's bottom surface, was used as an absorbing layer between the source and the suspended cells in order to energy regulate the alpha particles. The cells in suspension were allowed to settle to the polyester film surface, which positioned them approximately at the end-track of alpha particles emitted from the underlying source.

The alpha emitter is a commercially available source from Isotope Products. Energy regulation was achieved by passing the alpha particles through the uniform 12.7 $\mu$m thick polyester film layer, acting as the lower surface of the dish. Variation in the spacing of an air gap between the source and the dish, that serves as another energy absorbing layer, was used to fine tune the energy of emitted alphas such that their end-track occurred at the membranes of a monolayer of CHO cells resting on the polyester film.

The culture dish in which the CHO cells were grown was constructed of a 50 mm inner diameter of polytetrafluoroethylene (PTFE) (DuPont, Teflon™), or glass, ring to which 12.7 $\mu$m thick polyester film had been attached on the bottom surface of the ring, in order to form a radiation window as the bottom surface of the dish. A biologically compatible adhesive may be used. Dish and the polyester film were autoclaved for sterilization prior to filling with a suspension of cells.

Cells were suspended in either Ham's F12 growth media or phosphate buffered saline (PBS) at typically $5 \times 10^5$ to $2 \times 10^6$ cells/ml.

The dish was then placed onto the Cm-244 source, such that the polyester film was in close proximity to the source, with variable air gap between the polyester film and the titanium coating of the source. This provided the appropriate positioning of the settled cells, such that the lower portion of a monolayer of cells, and specifically their membranes were located at the end track of irradiated alpha particles from the Cm-244 source.

Cells in the dish were irradiated for 10–30 minutes, providing roughly 10–30 alpha particle impingements upon each cell's membrane. Each impingement created a damage site in the cell membrane to increase membrane fluidity at the damage site to electroporation material transport.

Cells were removed from the polyester dish.

Cells were resuspended in 0.8–1.0 ml HEPES buffered saline or phosphate buffered saline solution at approximately $1 \times 10^6$ cells/ml.

5–50 $\mu$g of plasmid DNA were added.

The resuspended cells and added plasmid DNA were electroporated at 600 V/cm–1000 V/cm for a pulse duration of 4–5 msec.

The cells were then seeded into growth media in culture dishes.

24–48 hours post electroporation, the cells were evaluated using a cytofluorograph (Becton Dickinson, Facstar+) to determine percent transfection efficiency.

Figures 3A, 3B:
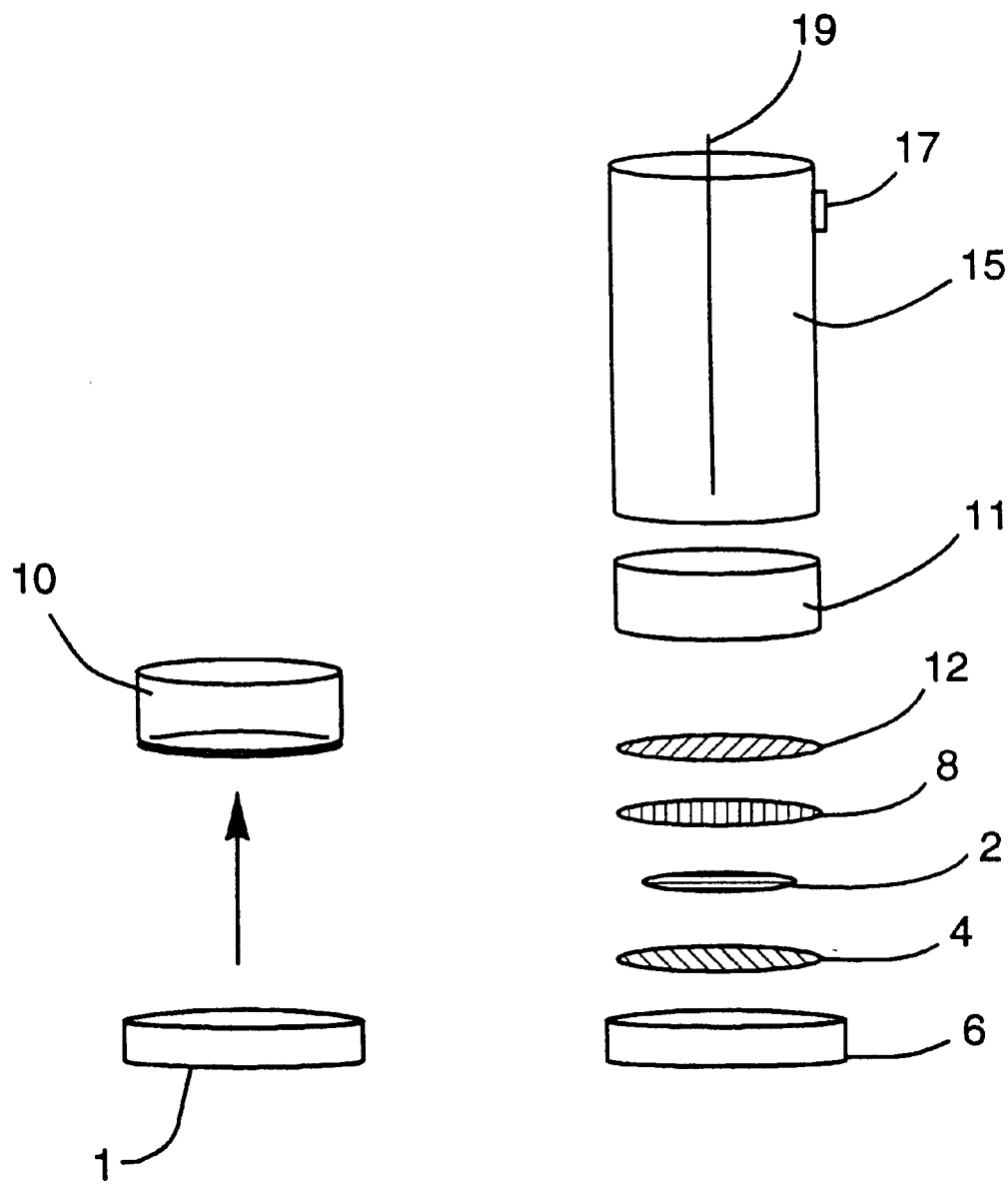
FIGS. 3A and 3B show an enlarged view of the alpha-emitting source and the polyester film/glass ring culture dish having a variable air gap for optimum alpha travel length and also illustrating an ionization chamber for experimental determination of optimal distance of the cells or structures in the culture dish from the source.

FIG. 3a and FIG. 3b show an enlarged view of the alpha-emitting source 1 comprising Cm-244 2 electroplated on a platinum substrate 4 housed in a stainless steel fixture 6 with an aluminum window & FIG. 3a and FIG. 3b also show in addition to the alpha-emitting source 1, a culture dish 10 in which the CHO cells are suspended with the dish being constructed of a 50 mm diameter glass or PTFE ring 11 to which a 12.7 $\mu$m thick polyester film (i.e. Mylar™) 12 has been attached with an adhesive or clamped on the bottom surface of the ring, in order to form the bottom surface of the dish. FIG. 3b also shows an ionization chamber 15 having a purge port 17 with an electrode 19 longitudinally disposed within the ionization chamber 15. The ionization chamber is used for experimental determination of optimal distance from the source (i.e., the farthest distance from the source where alpha activity may still be detected). FIG. 3a illustrates that there is a variable air gap between the source 1 and the dish 10 for optimum alpha travel length with the arrow illustrating normal alpha trajectory.

Figure 4:
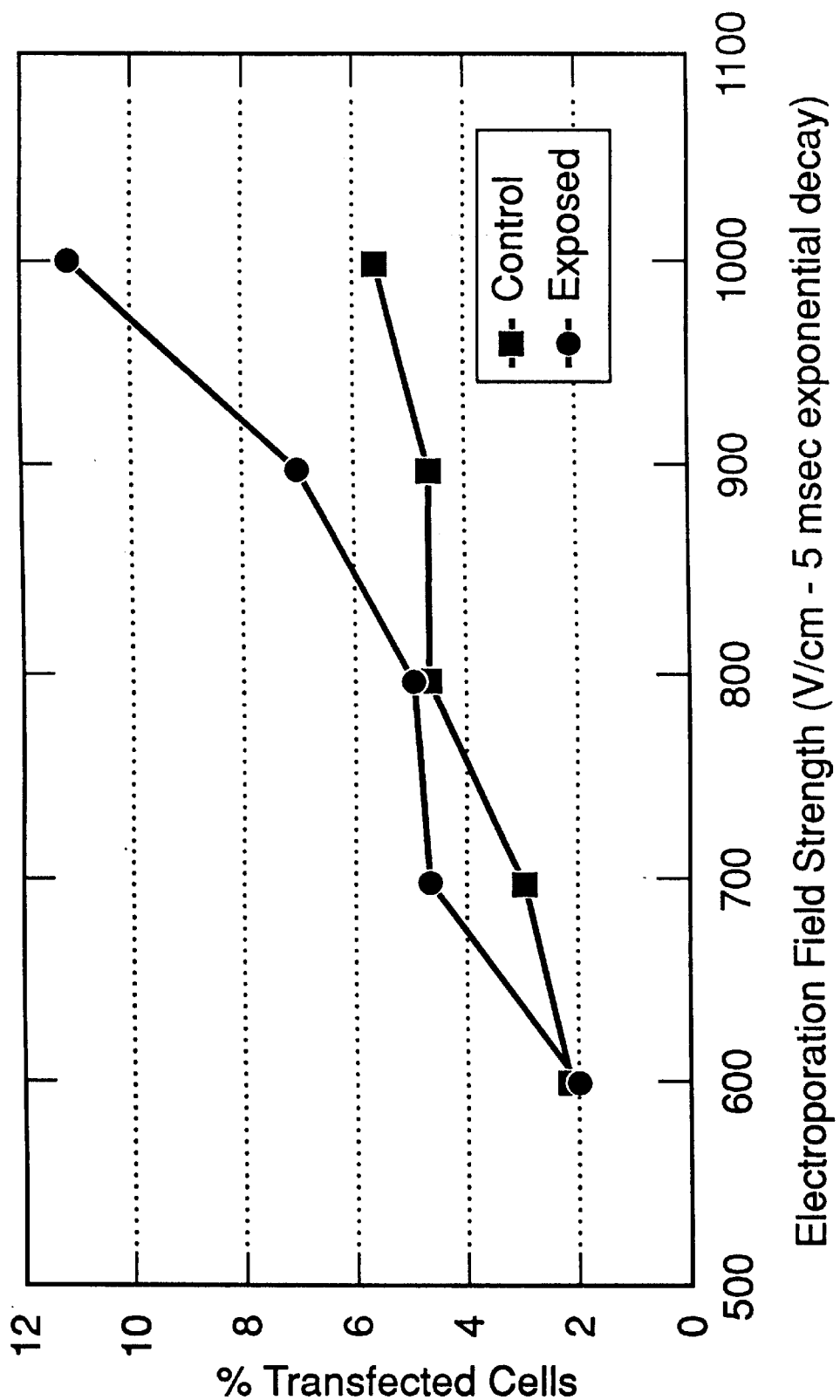
FIG. 4 shows the results of the CHO electroporation study of GFP expression as analyzed by a cytofluorograph.

FIG. 4 shows the results of the CHO electroporation study of GFP expression as analyzed by a cytofluorograph, indicating the increased transfection of irradiated cells vs. non-irradiated controls.

There are many different implementations of this specific technique, including variations on sources used, absorbing materials used, transfection techniques, electroporation protocols, target cells, and plasmid vectors.

The alpha emitting source may be fabricated by electrode-positing $7.4 \times 10^5$ to $1.5 \times 10^6$ Bq/mm$^2$ (2–4 mCi/cm$^2$) of Cm-244 onto one side of a platinum disk (30 mm in diameter by 500 $\mu$m thick). In this case, the active area of the Cm-244 is 25 mm in diameter and located at the center of the platinum disk. The disk is covered with a 12.5 $\mu$m sheet of aluminum foil and clamped into place into a machined stainless steel casing. The foil and stainless casing provided mechanical containment to the radioactive Cm-244. The aluminum foil sealed the source and provided an initial absorbing layer to reduce the energy of emitted alpha particles.

Other sources of alpha particles may also be employed, with either experimentation or mathematical modeling being used to determine the appropriate absorbing materials and their respective thicknesses which must be used to energy regulate the alpha particles such that their end track occurs in the target cell boundary and does not extend deeply into the target cell. Experimental methods to set this appropriate placement include use of an ionization chamber or surface barrier diode at the location where the cells will be positioned and adjustment of absorbing materials and their thicknesses around the point of loss of detected activity. Ionization event counting can then be used to determine how long a cell must be positioned at this location in order to experience a desired number of alpha impingements. Alternatively, mathematical modeling employing the Bethe and similar formulas and knowledge of a source's activity may be used to determine optimum placement and times for targets using a variety of absorbing materials between the source and target cells. Several computer programs (notably, TRIM© available from IBM) are available which can be used to assist performing this calculation.

Alternatively, as opposed to reducing the energy of an ionizing radiation particle by use of absorbing layers, a particle may be accelerated to a desired energy such that energy deposition occurs within and is limited to the target boundary.

Figure 5:
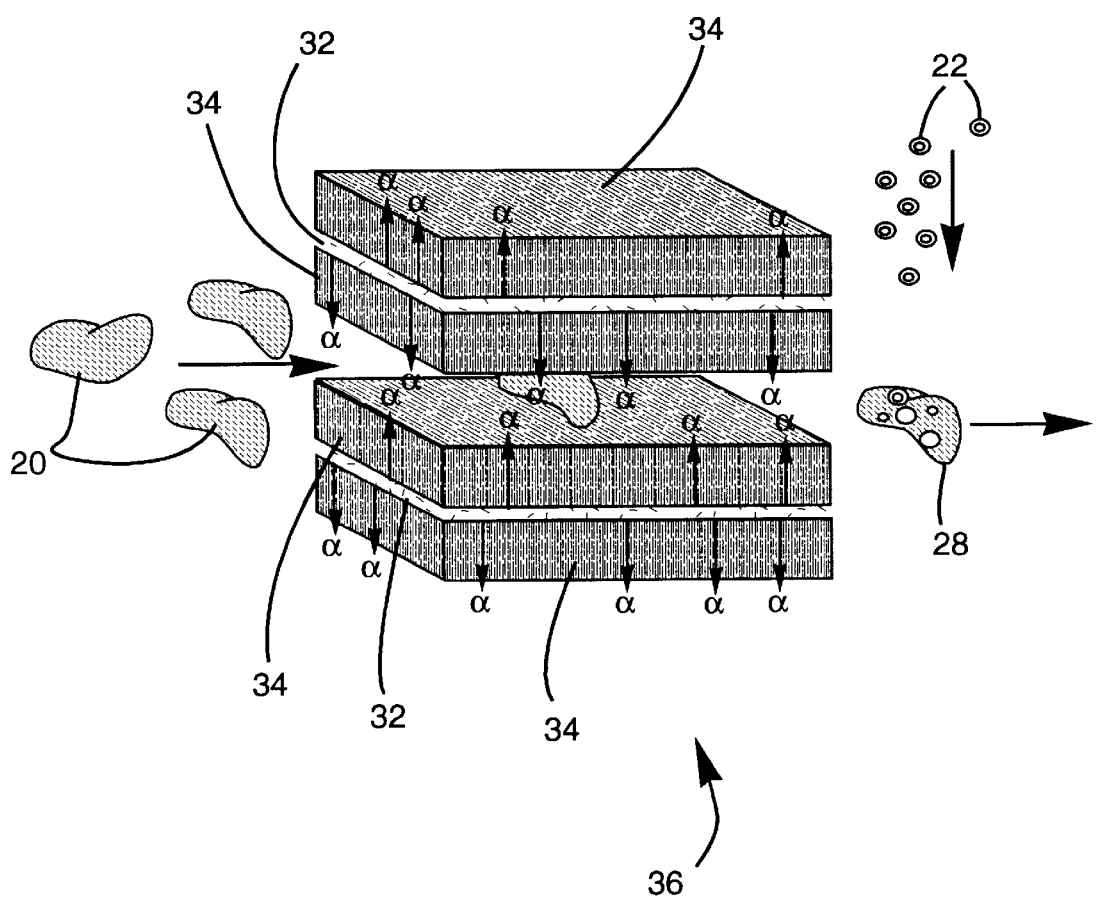
FIG. 5 shows an apparatus having microfluidic alpha-emitting plates coated with an energy-regulating layer to optimize alpha disruption in the vicinity of the cell boundary, providing inlet paths for genetic material.
Figure 6:
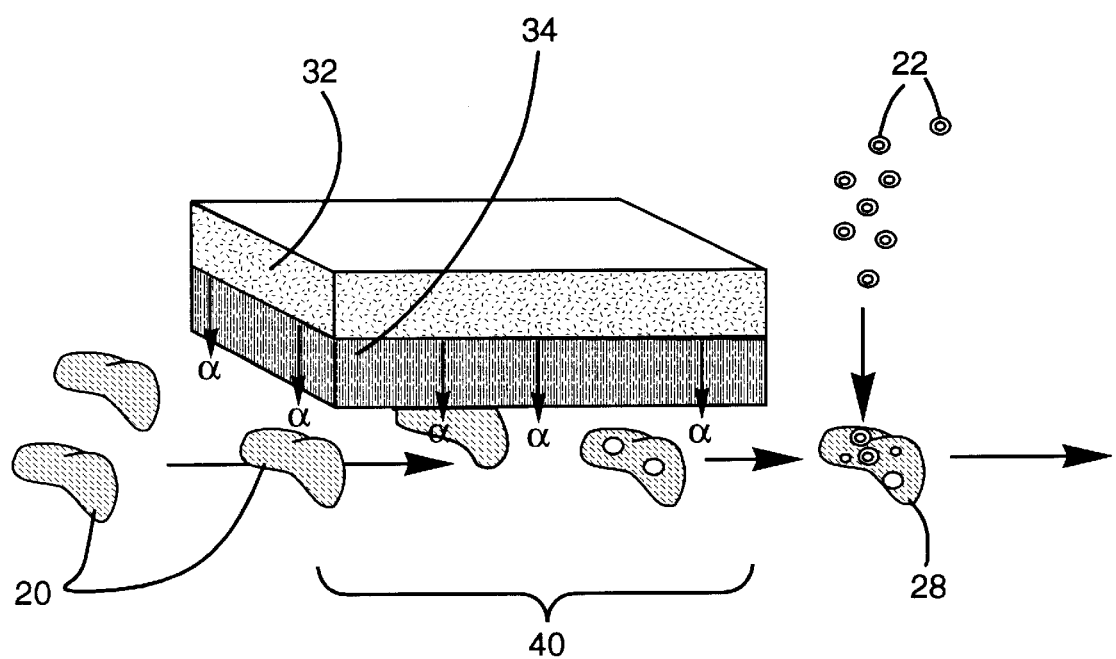
FIG. 6 shows an apparatus as in FIG. 5 having a microfluidic alpha-emitting layer coated with an energy-regulating layer showing the active disruptive zone to optimize alpha disruption in the vicinity of the cell boundary.

Many other embodiments to applicant's method are possible. In addition to the laboratory scale method for suspended cell irradiation and electroporation, a continuous feed bioreactor system is presented which enables the continuous processing of a flow stream of cells to be transformed. A microfluidic positioning of cells suspended in aqueous media may be used to optimize alpha-particle disruption of the cellular boundary of suspended cells. These suspended cells are made to flow through an energy-regulated radiation zone, using a variety of pumping techniques (i.e. hydrostatic pressure head, electro-osmotic pumping or mechanical pumping). Cells or structures in aqueous suspension are driven through the reactor while controlling the flowrate and the flow-dependent number of alpha-particle-induced disruptions upon the cell or structure boundary. The flowrate of the suspended cell containing fluid may be varied to control the number of alpha-particle impingements which occur to any given cell. Intermittent flow may be used to allow the cells to settle out of suspension onto an active radiation window as previously described. These impingements each create a localized cellular boundary disruption per Applicant's method. Downstream of the energy regulated radiation source, a plasmid flowstream intermingles with the aqueous cell suspension. Concurrent or subsequent use of electromechanical/chemical techniques, including electroporation, are employed to assist in further disruption of the cellular boundary to provide openings in the boundary for the purpose of introduction of plasmid vectors into the cells. FIG. 5 shows an apparatus having microfluidic alpha-emitting plates 32 coated on the top and bottom sides with an energy-regulating layer 34 to optimize alpha disruption in the vicinity of the cell boundary, providing inlet paths through temporary openings in the boundary of the target cell or structure for genetic material to be introduced therein. The target cell or structure flow 20, suspended in a flowstream, flows through the apparatus 36 and as the flowstream of target cells 20 flows through, the target cells or structures come in close contact with the coated alpha emitter 32 wherein localized disruptions are created within the boundary of the individual target cell or structure. Then the target cell or structure is subjected to further excitation in the boundary to create a temporary opening within the boundary of the cell or structure to allow foreign material 22, such as plasmids, suspended in a flowstream and flowing directly into the flowpath of the irradiated target cells or structures, so to be introduced through the opening in the boundary of the target cell or structure when the material comes in contact with the target cells or structures to produce transformed cells or structures 28 having desirable genetic traits. FIG. 6 again shows an apparatus having an alpha-emitter 32 coated with an energy-regulating layer 34 to optimize alpha disruption in the vicinity of the cell boundary. FIG. 6 illustrates the active disruption zone 40. The target cell or structure flow 20, suspended in a flowstream, flows through the apparatus and as the flowstream of target cells 20 flows through, the target cells or structures come in close contact with the coated alpha emitter 32 within the active disruption zone 40 wherein localized disruptions are created within the boundary of the individual target cell or structure. Then the target cell or structure is subjected to further excitation in the boundary to create a temporary opening within the boundary of the cell or structure to allow foreign material 22, such as plasmids, suspended in a flowstream and flowing directly into the flowpath of the irradiated target cells or structures, to be introduced through the opening in the boundary of the target cell or structure when the material comes in contact with the target cells or structures to produce transformed cells or structures 28 having desirable genetic traits.

Figure 7:
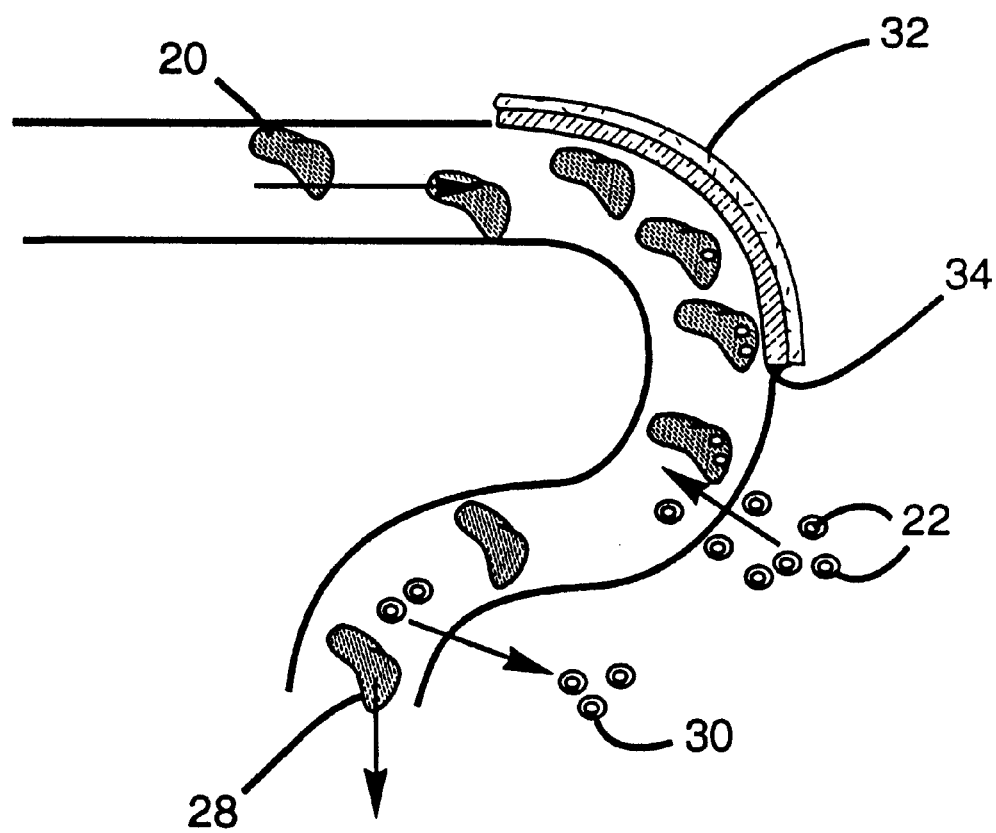
FIG. 7 shows a prototype reactor that handles a wide range of cell or structure sizes by centrifugally positioning cells or structures against an active irradiation surface.

Flexibility in design of the bioreactor prototype, as shown in FIG. 7, enables future seamless transfer of the application to other cell types, including animal, plant, bacterial and phages. FIG. 7 shows a prototype reactor that handles a wide range of cell or structure sizes by centrifugally positioning cells or structures 20 that are against an active irradiation surface comprising an ionizing particle emitter 32 coated with an energy-regulating layer 34. Subsequent delivery of foreign material 22, such as plasmids, into the flowstream of irradiated target cells or structures 20 incorporates cellular separation techniques to possibly recycle undelivered plasmid vectors 30. Transformed target cells or structures 28 are the resulting products.

Alpha particles are ideally suited to the method of the present invention. They are provided without extensive technology support, they do not require particle accelerators or other equipment and are available from natural sources. However, there are other energy-regulated radiation sources that can also be used to similar effect, such as accelerated heavy and light ions, beta sources, electron guns, etc.

Those skilled in the art will realize that ionizing particle radiations of specific energies will only have track lengths of up to approximately 50 μm in biological materials, including cellular membranes, cell walls, and other cellular boundary layers. For material delivery to structures having boundaries thicker than these tracklengths, iterative use of applicant's methodology may be required. For instance, for transformation of plant tissues, plasmid material must be delivered through a thick, waxy cuticular layer in addition to the cell wall of individual cells. Isotopic sources of alpha particles will typically create alpha particles with energies limited below 10 MeV, which can only travel up to approximately 50 microns in biological materials. However, by iteratively using applicant's method of radiating and digesting irradiated damage tracks, tunnels greater than 50 microns in depth may be created.

Another embodiment of the subject invention is to facilitate the introduction of genetic material into cells and to enhance the genomic incorporation of that material for the purpose of stable genetic transformation of cells. The enhancement of the genomic incorporation is accomplished by using ionizing radiation, separate from the energetic charged particles used to create localized disruption within the cellular boundary, to cause single-stranded breaks in the cellular genome. These singe-stranded breaks serve as insertion points for previously introduced genetic material.

Another embodiment of the present invention is to recursively apply this methodology to facilitate the introduction of genetic material into cells or structures to promote the repeated transient expression of gene products. This embodiment has application where it is desired to produce a given gene product, as encoded by the delivered genetic material, by the same cell for extended periods of time. Such repeated application of method would provide intact genetic material to the cell to replace genetic material denatured by cellular DNAase/RNAase activity. This embodiment is also applicable to the recursive introduction of pharmaceutical materials into cells or structures.

While there has been shown and described what are at present considered the preferred embodiments of the invention, it will be obvious to those skilled in the art that various changes and modifications can be made therein, without departing from the scope of the invention defined by the appended claims.

What is claimed is:

1. A method for creating a localized disruption through a boundary of a cell comprising the steps of:

a) generating a set of energetic charged particles;

b) exposing the boundary of the cell to said set of energetic charged particles, said energetic charged particles having regulated energy such that said charged particles have an amount of excess kinetic energy sufficient to disrupt atomic bonding thereby causing atomic bond rearrangement through said boundary of said cell thereby creating the localized disruption through said boundary of said cell, and as said excess kinetic energy is expend to create said localized disruption, said amount of excess kinetic energy drops to zero, thus said particles are unable to create further damage within said cell beyond said boundary.

2. The method of claim 1 wherein said energetic charged particles comprise at least one of alpha particles, beta particles, heavy ions, light ions or positrons.

3. The method of claim 2 wherein said alpha particles are derived from the spontaneous decay of an isotope selected from the group consisting of Ac-225, Ac-227, Am-241, Am-243, At-211, At-217, At-218, At-219, Bi-210m, Bi-211, Bi-212, Bi-213, Bi-214, Bk-247, Bk-249, Cf-249, Cf-250, Cf-251, Cf-252, Cm-242, Cm-243, Cm-244, Cm-245, Cm-246, Es-253, Es-254, Fm-254, Fm-255, Fr-221, Gd-148, Gd-150, Gd-152, Hf-174, Nd-144, Np-237, Pa-231, Po-210, Po-211, Po-211m, Po-212, Po-212m, Po-213, Po-214, Po-215, Po-216, Po-218, Pt-190, Pu-238, Pu-239, Pu-240, Pu-241, Pu-242, Ra-222, Ra-223, Ra-224, Ra-226, Rn-218, Rn-219, Rn-220, Rn-222, Sm-146, Sm-147, Th-226, Th-227, Th-228, Th-229, Th-230, Th-232, U-230, U-232, U-233, U-234, U-235, U-236 and U-238.

4. The method of claim 3 wherein said isotope is Cm-244.

5. The method of claim 1 wherein said boundary comprises cellular membrane, cell wall, nuclear membrane, organelle membranes or protein coats.

6. The method of claim 1 wherein said cell is mammalian, bacterial or a plant.

7. The method of claim 1 wherein said kinetic energy is in the range of 1–10,000 keV.

8. The method of claim 1 wherein said step b utilizes at least one layer of a material that reduces said excess kinetic energy of said energetic charged particles as a regulating means to regulate said energy of said energetic charged particles.

9. The method of claim 1 wherein said step b utilizes acceleration of an energetic charged particle as a regulating means to regulate said energy of said charged particle.

10. The method of claim 1 wherein said step b utilizes a natural isotopic source to produce energetic charged particles of specific energy.

11. The method of claim 1 wherein indirect ionizing radiation is used to produce energetic charged particles at a specific or subsequently regulated energy level.

12. A method for facilitating the introduction of a material into a cell comprising the steps of:

a) generating a set of energetic charged particles;

b) exposing the boundary of the cell or to said set of energetic charged particles, said energetic charged particles having regulated energy such that said charged particles have an amount of excess kinetic energy sufficient to disrupt atomic bonding thereby causing atomic bond rearrangement through said boundary of said cell thereby creating the localized disruption through said area of said boundary of said cell, and as said excess kinetic energy is expend to create said localized disruption, said amount of excess kinetic energy drops to zero, thus said particles are unable to create further damage within said cell beyond said boundary, c) disposing said material wherein said material is selected from the group consisting of genetic material, macromolecules, phages, and chemical species within close proximity to said cell, said material being of a size suitable for introduction into said cell;

d) exciting said area of said boundary of said cell where said localized disruption was created so to create a localized transient opening through said boundary to facilitate the introduction of material through said transient opening into said cell.

13. The method of claim 12 wherein said energetic charged particles comprise at least one of alpha particles, beta particles, heavy ions, light ions or positrons.

14. The method of claim 13 wherein said alpha particles are derived from the spontaneous decay of an isotope selected from the group consisting of Ac-225, Ac-227, Am-241, Am-243, At-211, At-217, At-218, At-219, Bi-210m, Bi-211, Bi-212, Bi-213, Bi-214, Bk-247, Bk-249, Cf-249, Cf-250, Cf-251, Cf-252, Cm-242, Cm-243, Cm-244, Cm-245, Cm-246, Es-253, Es-254, Fm-254, Fm-255, Fr-221, Gd-148, Gd-150, Gd-152, Hf-174, Nd-144, Np-237, Pa-231, Po-210, Po-211, Po-211m, Po-212, Po-212m, Po-213, Po-214, Po-215, Po-216, Po-218, Pt-190, Pu-238, Pu-239, Pu-240, Pu-241, Pu-242, Ra-222, Ra-223, Ra-224, Ra-226, Rn-218, Rn-219, Rn-220, Rn-222, Sm-146, Sm-147, Th-226, Th-227, Th-228, Th-229, Th-230, Th-232, U-230, U-232, U-233, U-234, U-235, U-236 or U-238.

15. The method of claim 12 wherein said genetic material comprises plasmid vectors, single or double stranded DNA or RNA.

16. The method of claim 12 wherein said macromolecules comprises fluorophores, proteins, enzymes, carbohydrates or lipids.

17. The method of claim 12 wherein said chemical species is a pharmaceutical.

18. The method of claim 12 wherein said boundary comprises cellular membrane, cell wall, nuclear membrane, organelle membranes or protein coats.

19. The method of claim 12 wherein said cell is mammalian, bacterial or a plant.

20. The method of claim 12 wherein said excitation step is electrical excitation.

21. The method of claim 20 wherein said electrical excitation is electroporation.

22. The method of claim 12 wherein said excitation step is mechanical excitation.

23. The method of claim 22 wherein said mechanical excitation is acoustic, dynamic pressure, or surface acoustic wave excitation.

24. The method of claim 22 wherein said mechanical excitation is ultrasonic excitation at and around said localized disruption.

25. The method of claim 22 wherein said mechanical excitation is mechanical agitation at and around said localized disruption.

26. The method of claim 22 wherein said mechanical excitation is a pressure differential across said localized disruption.

27. The method of claim 22 wherein said mechanical excitation is thermal excitation at and around said localized disruption.

28. The method of claim 22 wherein said mechanical excitation is laser excitation at and around said localized disruption.

29. The method of claim 22 wherein said mechanical excitation is concentration gradients across said localized disruption.

30. The method of claim 12 wherein said excitation step is chemical excitation.

31. The method of claim 30 wherein said chemical excitation is chemical etching of said localized disruption.

32. The method of claim 31 wherein said chemical etching is enzymatic digestion.

33. The method of claim 32 wherein said enzymatic digestion is protoplasting or partial protoplasting of plant cells.

34. The method of claim 30 wherein said chemical excitation is biochemical attack of said localized disruption.

35. The method of claim 34 wherein said biochemical attack of said localized disruption is bacterial infection or viral infection.

36. The method of claim 12 wherein said kinetic energy is in the range of 1–10,000 keV.

37. The method of claim 12 wherein said step b utilizes at least one layer of a material that reduces said excess kinetic energy of said energetic charged particles as a regulating means to regulate said energy of said energetic charged particles.

38. The method of claim 12 wherein said step b utilizes acceleration of said energetic charged particle as a regulating means to regulate said energy of said energetic charged particle.

39. The method of claim 12 wherein said step b utilizes a natural source to produce energetic charged prticles of specific energy.

40. The method of claim 12 wherein indirectly ionizing radiation is used to produce energetic charged particles at a specific or subsequently regulated energy level.

* * * * *